United States Patent
Wenzel et al.

(10) Patent No.: US 12,011,193 B2
(45) Date of Patent: Jun. 18, 2024

(54) PARTIALLY BLOCKED PEDICLE SCREW

(71) Applicant: Aesculap AG, Tuttlingen (DE)

(72) Inventors: Rudolf Wenzel, Nonnweiler-Primstal (DE); Hermann Backes, Nonnweiler-Primstal (DE)

(73) Assignee: Aesculap AG, Tuttlingen (DE)

( * ) Notice: Subject to any disclaimer, the term of this patent is extended or adjusted under 35 U.S.C. 154(b) by 260 days.

(21) Appl. No.: 17/620,172

(22) PCT Filed: Jun. 15, 2020

(86) PCT No.: PCT/EP2020/066476
§ 371 (c)(1),
(2) Date: Dec. 20, 2021

(87) PCT Pub. No.: WO2020/254243
PCT Pub. Date: Dec. 24, 2020

(65) Prior Publication Data
US 2022/0361927 A1    Nov. 17, 2022

(30) Foreign Application Priority Data
Jun. 17, 2019 (DE) .................... 10 2019 116 374.9

(51) Int. Cl.
*A61B 17/70* (2006.01)

(52) U.S. Cl.
CPC ...... *A61B 17/7038* (2013.01); *A61B 17/7032* (2013.01); *A61B 17/7037* (2013.01)

(58) Field of Classification Search
CPC ............ A61B 17/7038; A61B 17/7032; A61B 17/7037

(Continued)

(56) References Cited

U.S. PATENT DOCUMENTS

| 5,989,254 A | 11/1999 | Katz |
| 7,591,839 B2 | 9/2009 | Biedermann et al. |

(Continued)

FOREIGN PATENT DOCUMENTS

| CN | 1925804 A | 3/2007 |
| CN | 102525625 A | 7/2012 |

(Continued)

OTHER PUBLICATIONS

Search Report received in German Application No. 10 2019 116 374.9 dated Mar. 9, 2020, with translation, 11 pages.

(Continued)

*Primary Examiner* — Eduardo C Robert
*Assistant Examiner* — David C Comstock
(74) *Attorney, Agent, or Firm* — Christopher A. Rothe; Culhane PLLC

(57) ABSTRACT

A polyaxial pedicle screw has a screw shaft and a screw head with a substantially spherical base shape. The polyaxial pedicle screw is mounted in a receiving sleeve or area. An insertion sleeve can be pressed against the screw head to determine a relative pivot position between the receiving sleeve or area and the screw shaft. Two pivot guide or pivot restriction units each have at least one extension projecting radially and in the longitudinal direction of the screw beyond the spherical base shape of the screw head. The extensions form stops on their radial outer surfaces and are positioned to permit relative pivoting of the screw shaft and the area or receiving sleeve only in one pivoting plane, and to abut in a supporting manner against a radially inner circumferential side of the area or receiving sleeve during relative pivoting in another pivoting plane.

29 Claims, 5 Drawing Sheets

(58) Field of Classification Search
USPC ....... 606/266, 267, 270, 272, 305, 308, 319, 606/320, 325, 328

See application file for complete search history.

(56) References Cited

U.S. PATENT DOCUMENTS

| | | | |
|---|---|---|---|
| 7,837,709 | B2 | 11/2010 | Dutoit et al. |
| 8,048,133 | B2 | 11/2011 | Biedermann et al. |
| 8,926,669 | B2* | 1/2015 | Jacofsky ............ A61B 17/7076 606/264 |
| 9,060,811 | B2 | 6/2015 | Werner et al. |
| 9,138,261 | B2 | 9/2015 | Di Lauro et al. |
| 9,492,209 | B2 | 11/2016 | Biedermann et al. |
| 9,987,064 | B2 | 6/2018 | Jensen |
| 2005/0143823 | A1 | 6/2005 | Boyd et al. |
| 2005/0216003 | A1 | 9/2005 | Biedermann et al. |
| 2006/0200131 | A1* | 9/2006 | Chao .................. A61B 17/7037 606/328 |
| 2008/0119857 | A1 | 5/2008 | Potash et al. |
| 2008/0147129 | A1 | 6/2008 | Biedermann et al. |
| 2010/0036436 | A1 | 2/2010 | Winslow et al. |
| 2010/0305621 | A1 | 12/2010 | Wang et al. |
| 2011/0009911 | A1 | 1/2011 | Hammill, Sr. et al. |
| 2012/0053640 | A1 | 3/2012 | Trieu |
| 2013/0023935 | A1 | 1/2013 | Pham et al. |
| 2014/0121703 | A1* | 5/2014 | Jackson ............. A61B 17/7032 606/246 |
| 2014/0343617 | A1 | 11/2014 | Hannen |
| 2015/0282844 | A1 | 10/2015 | Vedula et al. |
| 2017/0245898 | A1* | 8/2017 | May ................... A61B 17/7032 |
| 2018/0132902 | A1 | 5/2018 | Wu et al. |
| 2019/0029731 | A1* | 1/2019 | Shoshtaev ............ A61B 17/861 |
| 2019/0183538 | A1* | 6/2019 | Lab .................... A61B 17/7032 |
| 2019/0223917 | A1 | 7/2019 | Gray et al. |

FOREIGN PATENT DOCUMENTS

| | | |
|---|---|---|
| CN | 104706405 A | 6/2015 |
| CN | 104902833 A | 9/2015 |
| EP | 1570796 A1 | 9/2005 |
| JP | 2008126066 A | 6/2008 |
| WO | 2014064249 A2 | 5/2014 |

OTHER PUBLICATIONS

Search Report received in International Application No. PCT/EP2020/066476 dated Oct. 23, 2020, with translation, 6 pages.
Written Opinion received in International Application No. PCT/EP2020/066476 dated Oct. 23, 2020, with translation, 15 pages.
Office Action received in Japanese Application No. 2021-575498 dated Jun. 17, 2022, with translation, 5 pages.
Search Report received in German Application No. 10 2019 116 368.4 dated Mar. 9, 2020, with translation, 10 pages.
Search Report received in International Application No. PCT/EP2020/066605 dated Oct. 30, 2020, with translation, 5 pages.
Written Opinion received in International Application No. PCT/EP2020/066605 dated Oct. 30, 2020, with translation, 9 pages.
Office Action received in Japanese Application No. 2021-575497 dated Nov. 9, 2023, with translation, 19 pages.
Office Action received in U.S. Appl. No. 17/619,732 dated Nov. 30, 2023, 14 pages.
Office Action received in Chinese Application No. 202080043769.5 dated Mar. 4, 2024, with translation, 16 pages.

* cited by examiner

PARTIALLY BLOCKED PEDICLE SCREW

CROSS-REFERENCE TO RELATED APPLICATIONS

This application is the national phase entry of International Application No. PCT/EP2020/066476, filed Jun. 15, 2020, and claims priority to German Application No. 10 2019 116 374.9, filed Jun. 17, 2019. The contents of International Application No. PCT/EP2020/066476 and German Application No. 10 2019 116 374.9 are incorporated by reference herein in their entireties.

FIELD

The present disclosure relates to a partially blocked pedicle screw (in short: screw) of the polyaxial type having a screw shaft and a screw head integrally connected thereto, which is rotatably and/or pivotably supported or received in a receiving sleeve (tulip).

BACKGROUND

Pedicle screws, in particular of the polyaxial type, are used in surgical procedures on the spinal column in order to fix the position of several vertebrae in relation to each other. The screws are each screwed into the pedicles of a vertebra and are connected via a connecting rod inserted into the screw heads or in the tulips connected to them. Depending on the application, screws with different degrees of freedom with regard to a relative movement between a tulip and a screw shaft are used. For example, for derotation of deformed spinal columns, screws are provided in which a pivot movement between the tulip and the screw shaft is blocked in the medial-lateral direction (i.e., in the lateral direction with respect to a spinal column or the associated human body), but is permitted in the cranial-caudal direction (i.e., in the longitudinal direction or height direction with respect to the spinal column) for positioning during surgery. This is achieved by making the screw head non-circular, e.g. with lateral flattenings, and an inlay or insert inserted into the tulip for axial application of pressure to the screw head for fixing the relative position between the screw and the tulip is designed with corresponding lateral inner surfaces which come into contact with the flattenings on the screw head.

Such pedicle screws are implanted using a special instrument or instrument set, which is usually standardized for a number of different pedicle screws.

From the prior art, for example from US 2010/0305621 A1 and U.S. Pat. No. 9,138,261 B2, a polyaxial pedicle screw is known in each case whose round head inserted in a receiving body is at least partially flattened on two opposite sides, so that a bushing (inlay/insert for axial insertion in a tulip) arranged proximally to the head has two ear-shaped axial projections which form flat inner surfaces, are guided with these inner surfaces on the flattened sides of the head and permit pivoting of the screw shaft and screw head relative to the bushing only in a plane parallel to the flat inner surfaces. Part of the head of the pedicle screw may protrude radially beyond the flattened sides to provide additional screw diametrical support of the screw head on the receiving body. However, this limits an achievable pivoting angle and reduces the guiding surface. Furthermore, the flanges are slightly elastically deformable. Accordingly, high lateral forces may not be adequately supported.

U.S. Pat. No. 8,048,133 B2 discloses a polyaxial pedicle screw, whose round head is machined on two screw-diametrically opposite sides in order to form a screw-diametrically extending cylinder, which comes proximally into contact with a corresponding surface of a pressure element (inlay/insert) and together with this surface forms a kind of sliding bearing, which allows rotations about a cylinder axis and blocks rotations/pivot movements about other axes. However, this blocking of rotation or pivoting about other axes is likely to be insufficiently stable at high lateral forces and will lead to rapid wear or deterioration of the connection.

A further document, U.S. Pat. No. 5,989,254 A, shows a polyaxial pedicle screw with a spherical head in which a cylindrical saddle surface or a transverse slot with a saddle-shaped, longitudinally curved slot base is recessed to receive a connecting rod via which several pedicle screws are connectable. In the case where a tulip is placed over the screw head of the pedicle screw and a connecting rod is inserted transversely into the tulip, the saddle surface rolls off the connecting rod when the screw head is pivoted in the tulip about an axis running diametrically to the screw. Transverse forces are mainly transmitted via an outer surface of the connecting rod and side surfaces of the recess for the saddle surface, i.e. via a relatively short line contact. This construction is prospectively not sufficiently stable against high transverse forces.

In summary, known solutions in many application situations are not capable of absorbing sufficiently high transverse loads when transverse pivoting is blocked (i.e., the permitted transverse forces are too low). Furthermore, these solutions have too many individual parts of the polyaxial pedicle screw and/or contain joints and are therefore complex to manufacture and to assemble. In particular, the internal geometry of the insert or insertion piece or retaining piece inserted proximally in the screw head within the tulip is often complex. This increases the manufacturing costs, among other things. Implantation of these screws may also require a separate set of instruments, which further increases the associated manufacturing costs due to lower quantities.

SUMMARY

The present invention is based on an object to reduce or avoid disadvantages of the prior art. In particular, a simple, stable pedicle screw with a screw head is to be provided that is pivotable within a receiving sleeve or tulip in one (single) screw-diametral direction (in particular cranial-caudal) and is fixed in position in another screw-diametrical direction (in particular medial-lateral) even with high transverse forces/side loads of at least 500N. Furthermore, with the present pedicle screw, in particular the instrumentation and set screws for fixing the screw, which should preferably be able to be loosened and tightened several times, of the same systems should be usable. In other words, the basic functions and the external geometry of the 'normal' (same system) polyaxial pedicle screw are to be retained.

The basic idea of the present invention is essentially to provide additional support/bearing/guide areas in the pedicle screw according to the invention between a receiving sleeve or tulip and a screw head mounted therein, which prevent transverse pivoting of the receiving sleeve or tulip relative to a screw shaft, which is integrally connected distally to the screw head, when a transverse load occurs. On the other hand, these additional support areas should not impede the mobility of the screw head relative to the receiving sleeve or tulip of the pedicle screw about a pivot axis. According to the invention, extensions projecting beyond the preferably spherical screw head are provided, which form these additional support surfaces and which can be or are brought directly into support/bearing/guide contact with the receiving sleeve. In this way, the screw head is not only secured against transverse rotation, as is usual with polyaxial pedicle screws, via a support area between the screw head and an insertion sleeve/inlay/insert arranged proximal to the screw head in the receiving sleeve or tulip, with said insertion sleeve/inlay/insert serving to press against the screw head and thereby fix its relative position in the receiving sleeve/tulip. Instead, the extensions are provided to form an additional support area with the receiving sleeve/tulip to prevent such transverse pivoting. Preferably, further support areas may also be provided which are oriented in different directions, such as a cylindrical surface extending transversely to the longitudinal axis of the screw, in order to always absorb the transverse load as optimally as possible.

More precisely, the object of the invention is solved by a pedicle screw of the polyaxial type, which has a screw shaft, at the proximal end of which a screw head with a substantially spherical basic shape is formed in one piece, which is mounted in a receiving sleeve or tulip, in which an insertion sleeve is inserted, which can be pressed against the screw head to fix a relative pivot position between the receiving sleeve or tulip and the screw shaft. Two diametrically opposite pivot guide units or pivot restriction units are provided, each having at least one extension projecting radially and in the longitudinal screw direction beyond the spherical basic shape of the screw head, the extensions forming stops on their respective, preferably partially cylindrical, radial outer surfaces. The extensions are positioned in such a way that they permit relative pivoting of the screw shaft and the tulip or receiving sleeve only in the pivot plane and that, in the event of relative pivoting in another pivot plane (transverse pivoting), they abut against a radially inner circumferential side of the tulip or receiving sleeve in a supportive manner. The support areas/stops created in this way between the screw head and the receiving sleeve/tulip mean that very high lateral loads (at least 500N) can be transmitted and lateral pivoting can be effectively blocked. Consequently, high lateral stability is achieved through thick extensions or guide tabs.

Furthermore, no changes to the outer geometry of the overall screw are necessary, which is why standard instruments of the same system can be used for implantation of the pedicle or bone screw. Accordingly, for such a pedicle screw, only internal changes to the screw construction are made in comparison with a standard screw of the same system, without the need for complex internal geometry on the insert. The insertion sleeve (insert/inlay) may be used essentially geometrically unchanged or with only relatively minor changes for both a uniplanar screw and a polyaxial screw, which is why higher quantities and lower costs may be achieved. Furthermore, the assembly process has to be changed minimally or even not at all, which is why no change in assembly is necessary. The number of parts required (receiving sleeve/tulip/body, insertion sleeve/insert/inlay and screw head and screw shaft) is also low. Furthermore, the individual components, i.e. the screw head, the insertion sleeve (inlay/insert) and the receiving sleeve (tulip), have a simple shape, which makes the pedicle screw easy to manufacture.

Preferably, the extensions proximally form partially cylindrical bearing surfaces which guide the relative pivoting of the screw shaft and of the tulip or receiving sleeve in the pivot plane and which are guided in the proximal direction on frontal or distal, correspondingly partially cylindrical recesses of the insertion sleeve in order to interact in the manner of a plain bearing. A pair of active surfaces formed in this way serves both to guide the pivoting about the pivot axis evenly and with as little friction as possible and in order to support or block the transverse pivoting, in particular about an axis transverse to the pivot axis. Since the extensions are diametrically opposite each other, a lever is also created between the at least two extensions or the corresponding bearing surfaces, via which transverse forces acting on the screw can be transmitted particularly well. Accordingly, pivoting of the screw head relative to the receiving sleeve/tulip about an axis transverse to the pivot axis can be effectively blocked.

It has proven expedient that the tulip or receiving sleeve has, on an inner circumferential surface, at least two diametrically opposite cavities, which are sufficiently large to accommodate the extensions in any pivot position. Without these cavities, pivoting of the screw head relative to the receiving sleeve/tulip would not be possible or would only be possible to a minor extent due to the extensions. Accordingly, the pivotability of the screw head in the receiving sleeve/tulip is ensured in particular by the cavities. Preferably, the cavities and the extensions are dimensioned and positioned in such a way that the extensions can abut against the radially inner circumferential side of the tulip or receiving sleeve in any pivoting position. This can be achieved, for example, in that the cavities are essentially rectangular. This provides a large stop surface or contact surface in the receiving sleeve/tulip, in particular one extending in the longitudinal screw direction, for the extensions of the screw head, whereby high transverse forces (at least 500N) can be transmitted directly and stably to the receiving sleeve/tulip. Accordingly, an interaction between the extensions of the screw head and the receiving sleeve and, as described above, an interaction between the extensions of the screw head and the insertion sleeve can effectively prevent pivoting about an axis transverse to the pivot axis.

It is advantageous if the extensions block pivoting of the screw head in a medial-lateral direction and allow pivoting in a cranial-caudal direction. This is advantageous in particular in the field of spinal rotation. In terms of construction, this is achieved by the fact that the receiving sleeve or tulip and preferably the insertion sleeve has, offset in the circumferential direction by 90° with respect to the extensions arranged therein in the assembled state, preferably U-shaped slots for receiving a connecting rod via which a plurality of pedicle screws can be connected to each other. In principle, this can also be provided in reverse for other application purposes. This means that various orientations of the screw head relative to the receiving sleeve/tulip are possible. Furthermore, in the pedicle screw, it should preferably be possible to pivot the screw shaft relative to the receiving sleeve or tulip in one pivot plane by at least +/−22°, preferably at least +/−30°. This range is also based on values that are advantageous for spinal rotation.

According to an advantageous embodiment of the invention, a diameter of the proximal bearing surfaces of the extensions is smaller than a diameter of the spherical basic shape of the screw head. That is, the extensions are arranged substantially crescent-shaped or ear-shaped on the spherical basic shape of the screw head (in particular in the vicinity of its screw-diametrical outer circumference), wherein a round part of the crescent or ears is oriented in the proximal direction. The diameter of the spherical basic shape of the screw head, in particular an outer contour of the entire screw head, is in this case preferably smaller than or equal to an inner diameter of the receiving sleeve/tulip. As a result, only a few corners and edges are formed on the screw head, which simplifies its manufacture and, if applicable, sterilization. Furthermore, the amount of machine finishing required for the receiving sleeve/tulip is minimized.

Preferably, additional support lugs are formed on the screw head, which are screw-diametrically offset inwards with respect to the extensions and which project beyond the extensions in the proximal direction. In particular, these support lugs are intended to form proximally partially cylindrical second bearing surfaces in order to interact with frontal, correspondingly partially cylindrical slots of the insertion sleeve in the manner of a plain bearing. A diameter of the second bearing surfaces is larger than that of the above-described first bearing surfaces of the extensions. This means that additional surfaces may be provided for guidance and force transmission during the intended pivoting movement and transverse loads are better supported.

For example, it may be advantageous if the support lugs are screw-radially flat on the outside and possibly also on the inside in order to support themselves on corresponding surfaces of the slots to block pivoting in the other pivot plane or the transverse pivoting. That is, the support lugs form a screw-diametrically flat surface on the screw head to provide an additional radial support area or guide area for transmitting lateral loads.

According to a further advantageous embodiment of the invention, the extensions may project screw-diametrically outwards and preferably proximally beyond an outer diameter of the spherical base body of the screw head. In other words, this screw-diametric widening of the screw head provides a lever between the two extensions or the bearing surfaces formed by them. Accordingly, even greater transverse loads can be supported via the bearing surfaces of the extensions of the screw head than according to the afore-described first advantageous embodiment.

Furthermore, an outer contour of the entire screw head (i.e., the spherical base body and the extensions projecting screw-diametrically beyond it) may be larger than the inner diameter of the tulip or receiving sleeve. Accordingly, it is useful if the cavities are formed by an undercut recessed in an inner circumferential wall of the receiving sleeve/tulip, which is preferably rectangular, further preferably square, in order to be able to accommodate the extensions. In principle, other configurations are also possible. In the case of a square undercut, however, it may be advantageous for the sleeve to be mounted rotated by 90° to allow the screw head to be moved in the same receiving sleeve/tulip in different (pivot) directions.

In particular, the extensions are supported in the undercut formed by the cavities in the receiving sleeve or tulip both in the screw-diametrical direction outwards and in the longitudinal screw direction. In other words, the cavities are embedded in an inner circumferential surface of the receiving sleeve/tulip in such a way that they form stops or support surfaces both in the screw-diametrical direction and in the longitudinal screw direction. Accordingly, in this embodiment, the cavities not only guide or support the extensions of the screw head in the screw-diametrical direction, but also guide or support them in the longitudinal screw direction. This means that all relative movements of the screw head are guided or supported both via the insertion sleeve (inlay/insert) and via the receiving sleeve/tulip, and the loads to be transmitted are distributed. Accordingly, the stiffness of the support of the screw head is further increased in the case of transverse loads.

Preferably, the extensions are each screw-radially flat on the inside and are guided on opposite surfaces of the recesses. This means that in this configuration the extensions form both the stops directed radially or screw-diametrically outwards and the guide surfaces directed radially or screw-diametrically inwards. If required, these may also assume additional support functions. The extensions are therefore designed to provide both the advantages of the crescent-shaped extensions and the advantages of the support lugs described above. As a result, the rigidity of the support of the screw head under transverse loads can be further increased.

Alternatively or additionally, in any of the aforementioned embodiments of the invention, a part of the screw head may be cylindrically milled off to provide a further bearing surface on the screw head, which interacts as a sliding bearing with corresponding bearing surfaces formed on the front side of the insertion sleeve or on the insert/inlay.

In summary, the object underlying the invention can be achieved by attaching lateral lugs to the head end of a bone screw/pedicle screw and corresponding interior spaces to a receiving sleeve or body or tulip, and by corresponding cavities to the insert as well. The lugs are supported both on the insert and on the body in the lateral direction and block movement in the lateral direction while at the same time allowing free movement in the cranial-caudal direction. The screw head and the lugs form a unit and have a cylindrical contour on the outside. Due to the design according to the invention, no additional connecting elements such as pins, axes and the like are necessary. For assembly of the entire pedicle screw (according to one embodiment, see the third embodiment described below), the bone screw may be assembled without tools via a rotational movement of the screw relative to the body, despite an outer diameter of the lugs that is larger than the inner diameter of the body. Due to the larger lug diameter, the screw is not only supported radially on the body during use, but also axially via the end faces of the lugs.

BRIEF DESCRIPTION OF THE DRAWING FIGURES

The present invention is described below based on preferred embodiments, which are described below by way of illustration. It should be noted that features of different embodiments may be combined and various modifications may be made without departing from the scope of protection of the invention.

DETAILED DESCRIPTION

Figure 1:
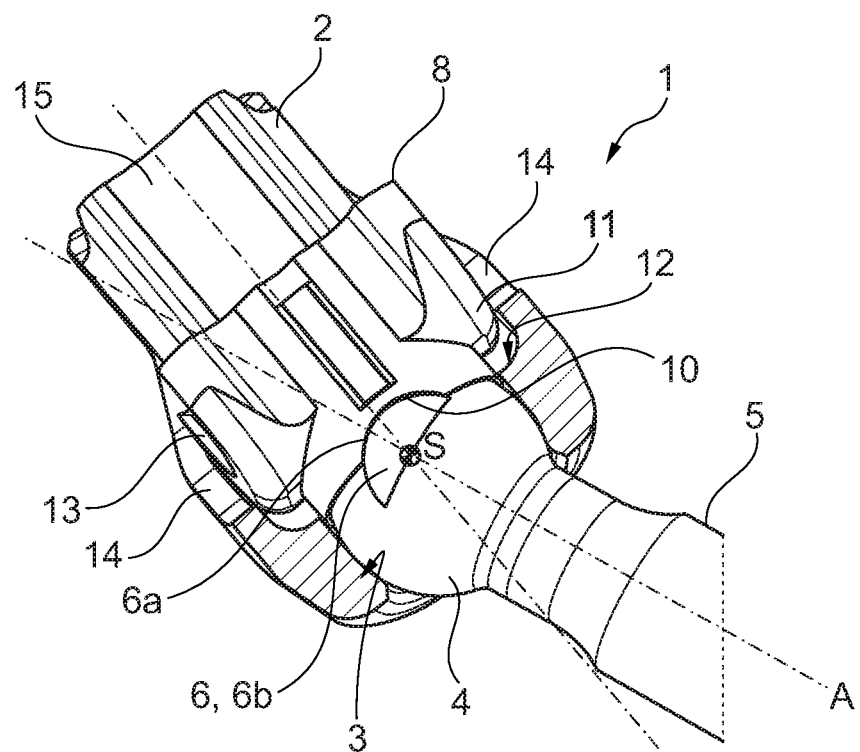
FIG. 1 shows a perspective, partial sectional view of the pedicle screw according to a first embodiment of the invention.

FIG. 1 shows a perspective, partial sectional view of a pedicle screw 1 according to the invention in an angled state. The pedicle screw 1 has a tulip or receiving sleeve 2, which is longitudinally cut in this representation and whose inner circumference is chronically narrowed at a distal end to form a contact surface 3 for a spherical screw head 4 of the pedicle screw 1. The pedicle screw 1 was inserted into the receiving sleeve 2 from the proximal direction in such a way that the spherical screw head 4 rests distally against the contact surface 3 and a screw shaft 5 integrally formed therewith projects distally from the receiving sleeve 2, so that the screw head 4 and the screw shaft 5 can be pivoted relative to the receiving sleeve 2.

The screw head 4 is also designed to be at least partially spherical proximally and also has two extensions 6 on screw-diametrically opposite sides, which extend from an outer circumference of the screw head 4 in a crescent shape in the proximal direction. I.e., distally oriented surfaces of the extensions 6 form bearing surfaces 6a, which serve to support the screw head 4 on an insertion sleeve 8 (inlay/insert). In the pedicle screw 1, these bearing surfaces 6a or their diameter define a pivot axis S about which the screw head 4 can be pivoted in relation to the receiving sleeve 2. In order to illustrate this, the pedicle screw 1 in FIG. 1 is shown in a pivoted state, which is made clear by the longitudinal axes of the screw shaft A and the receiving sleeve B intersecting at a pivot axis, i.e. the center axis of the bearing surfaces 6a. In addition, the extensions 6 form a preferably semi-cylindrical radial outer surface or a preferably semi-cylindrical radial stop 6b, which serve as a support surface for supporting the screw head 4 on the receiving sleeve 2.

Figure 4:
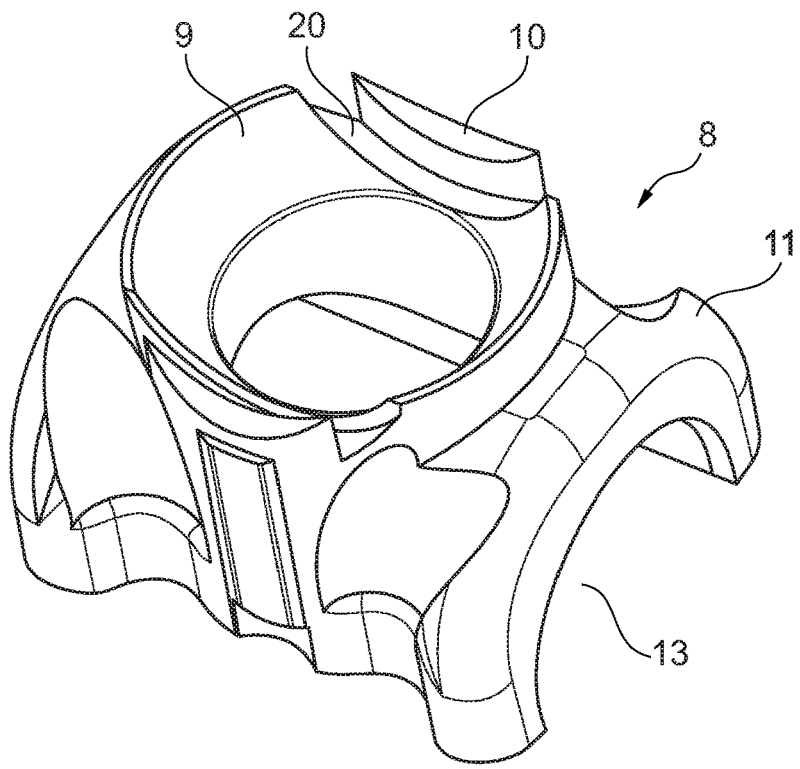
FIG. 4 shows an insertion sleeve according to the second embodiment of the invention.
Figure 8:
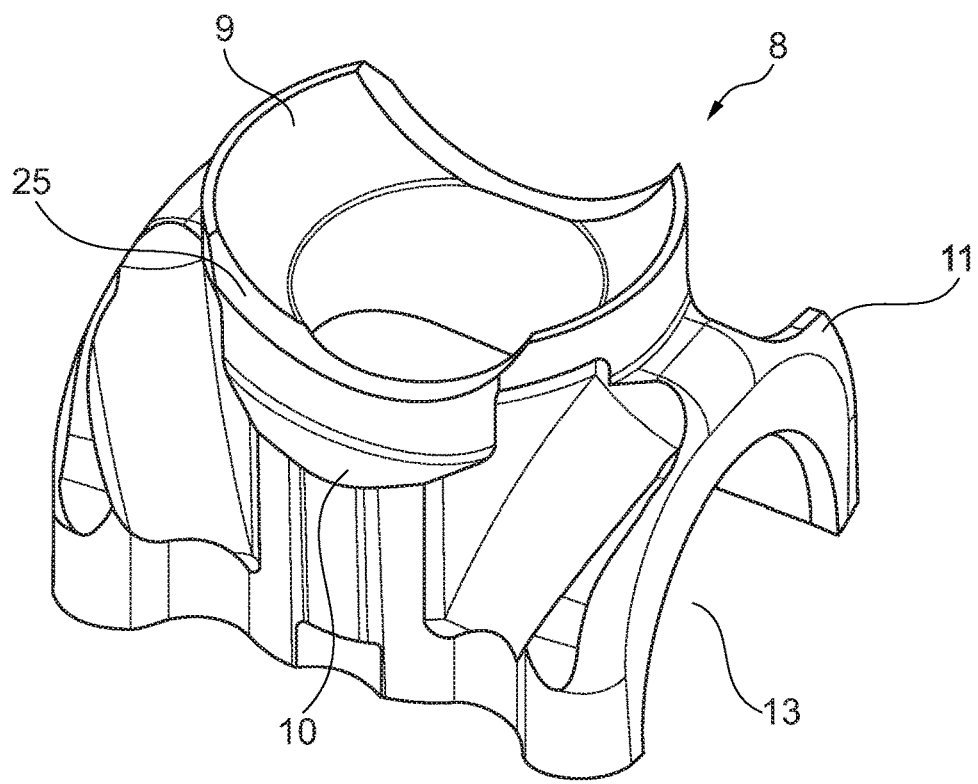
FIG. 8 shows an insertion sleeve according to the third embodiment of the invention.

The insertion sleeve 8 partially forms a hollow-spherical receiving surface 9 on its distal side for receiving the round screw head 4, which is not shown here but essentially corresponds to the corresponding receiving surface 9 of FIG. 4 and FIG. 8. Furthermore, a frontal, distal edge of the insertion sleeve 8 is not continuous, but has two diametrically opposite recesses 10, which correspond to the crescent-shaped or ear-shaped extensions 6, or more precisely, their bearing surfaces 6a. The recesses 10 interact with the bearing surfaces 6a in the manner of a plain bearing to ensure pivotability of the receiving sleeve 2 and the screw head 4.

At a proximal region of the insertion sleeve 8, it has two lateral bulges 11 offset by 90° to the recesses 10, which are received in corresponding saddle surfaces 12 within the receiving sleeve 2 in a predetermined position. The insertion sleeve 8 furthermore has a semi-cylindrical opening 13, which extends through the bulges 11 for receiving a connection rod, via which two pedicle screws 1 can be connected to each other during implantation or surgery. The receiving sleeve 2 furthermore has, at the same angular position as the saddle surfaces 12, two U-shaped slots 14 introduced from the proximal side, into which the connection rod is insertable. A thread 15 is provided at a proximal area within the receiving sleeve 2, into which a set screw can be screwed for tensioning the pedicle screw 1 and the connection rod.

Figure 2:
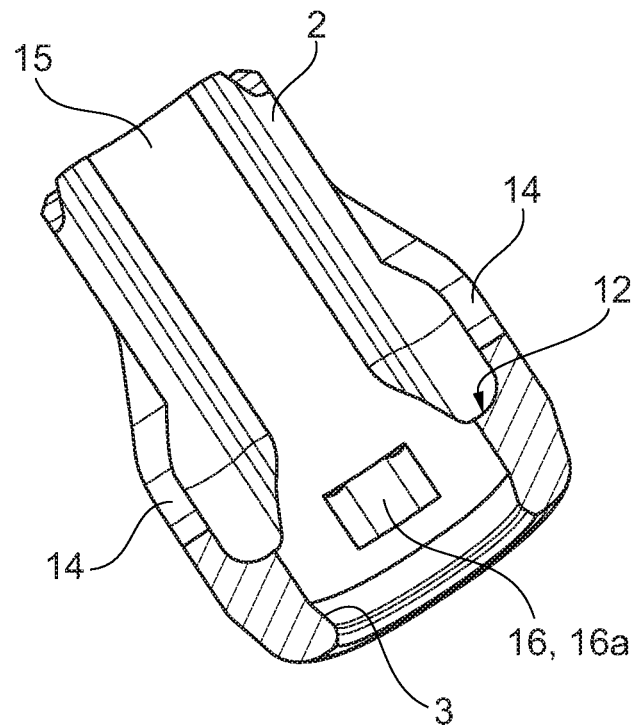
FIG. 2 shows a receiving sleeve or tulip in the longitudinal section according to the first embodiment.

FIG. 2 shows a longitudinal section of the receiving sleeve 2 according to the first embodiment of the invention. In addition to the features already described above, it is apparent from this view that in an inner circumferential region of the receiving sleeve 2, in which the screw head 4 is received, two cavities 16 (only one shown here) are provided diametrically opposite each other. These cavities 16 serve to receive the extensions 6 in order to ensure the mobility or pivotability of the screw head about the pivot axis S. At the same time, the cavities 16 form a support surface or stop surface 16a in order to support the screw head 4 directly on the receiving sleeve 2 via the extensions 6, or more precisely, via the radial stops 6b.

The second embodiment of the invention shown in FIG. 3 to FIG. 6 corresponds to a large extent to that of the first embodiment, which is why only their differences are discussed below and the same reference signs are used for similar features.

Figure 3:
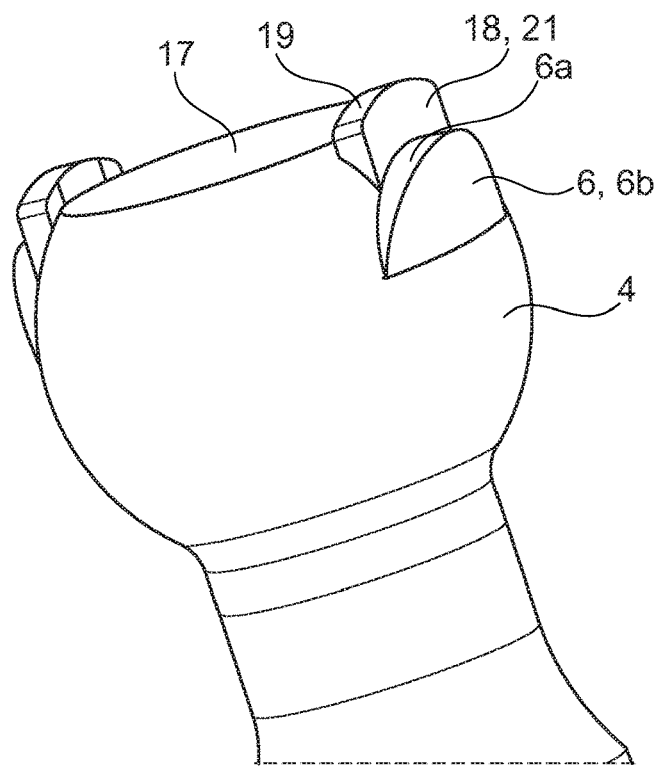
FIG. 3 shows a screw head according to a second embodiment of the invention.

FIG. 3 shows a perspective view of the screw head 4 according to the second embodiment of the invention. Here it can be seen that the screw head 4 has a proximal front surface 17, in which, for example, a tool receptacle or a channel for pressing in bone cement may be embedded. Such a front surface 17 may also be provided in the first embodiment. Furthermore, in addition to the extensions 6, the screw head 4 has support lugs 18 which are offset radially inwards. These support lugs 18 extend proximally beyond the proximal front surface 17 of the screw head 4 and also form at their proximal end lateral surfaces of the cylinder or second bearing surfaces 19 in order to form a further guide surface or support surface or bearing surface for guiding or supporting or bearing on the insertion sleeve 8. In the screw-diametrical direction, the support lugs 18 are formed flat on both sides.

FIG. 4 shows an insertion sleeve 8 according to the second embodiment of the invention. In addition to the receiving surface 9 and the recesses 10, this insertion sleeve distally has embedded slots 20 which are offset radially inwards relative to the recesses 10. This means that a position of the slots 20 corresponds to a position of the support lugs 18. Accordingly, in the distal direction, the slots 20 form an inner cylindrical surface, which interacts with the support lugs 18, more precisely, with the lateral cylinder surface or the second bearing surface 19 of the support lugs 18, in the manner of a plain bearing.

Figure 5:
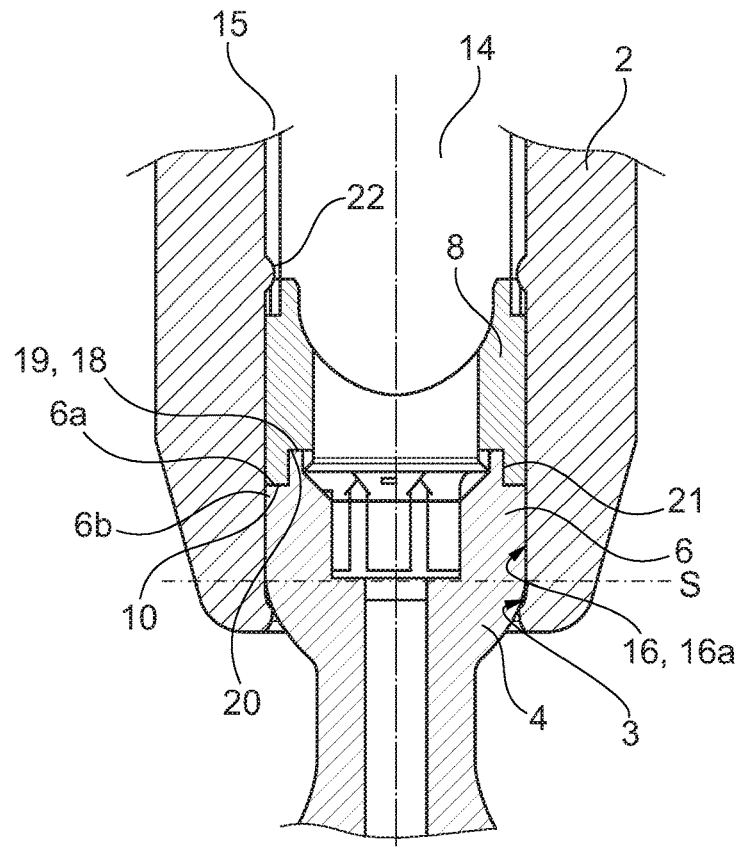
FIG. 5 is a longitudinal sectional view of the assembled pedicle screw according to the second embodiment of the invention.

FIG. 5 shows an assembled pedicle screw 1 according to the second embodiment in a longitudinal section. It can be seen how the extensions 6 of the screw head 4 rest screw-diametrically on the receiving sleeve 2, more precisely, on the support surfaces or stop surfaces 16a of the cavities 16, in order to be supported in the screw-diametrical direction. Furthermore, it can be seen that the bearing surfaces 6a of the extensions 6 of the screw head 4 and the recesses 10 of the insertion sleeve 8, as well as the second bearing surfaces 19 of the support lugs 18 and the slots 20 of the insertion sleeve 8, abut against each other in order to support and guide the screw head 4 in longitudinal screw direction against the insertion sleeve 8. Furthermore, it can be seen that the support lugs 18 are supported at least with the radially outer flat side 21 against corresponding side walls of the slots 20 in order to increase the stability of the pedicle screw 1 against pivoting in a direction transverse to the intended pivot axis S (transverse pivoting). Furthermore, according to this embodiment, two diametrically opposite stop projections 22 are provided in the receiving sleeve 2, offset by 90° to the slots 14, which serve to hold the insertion sleeve 8 provisionally (i.e., as long as the connection rod has not yet been inserted and the set screw has not yet been screwed in) in the receiving sleeve 2.

Figure 6:
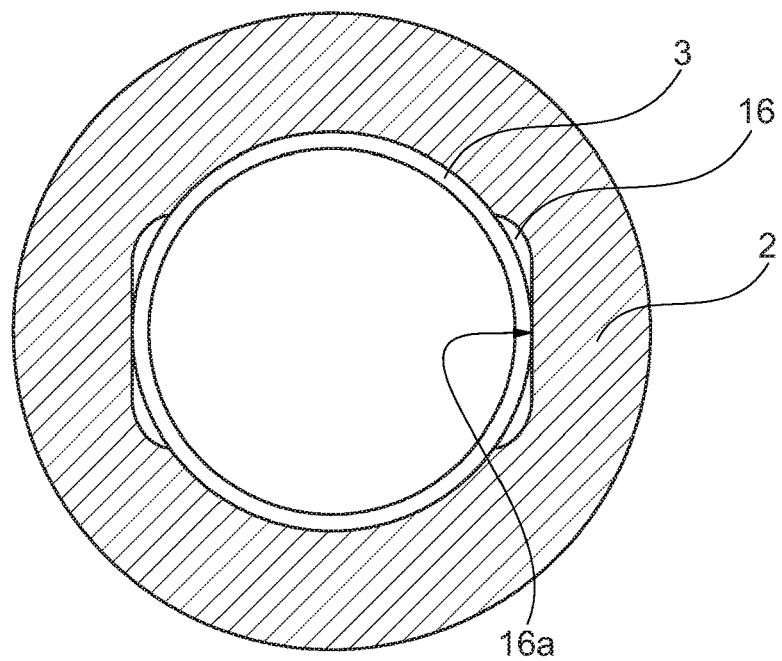
FIG. 6 is a cross-sectional view of the receiving sleeve according to the second embodiment in the region of the cavities.

FIG. 6 shows a cross-section of the receiving sleeve 2 in the area in which the screw head 4 is received. In particular, this illustration shows the shape of the cavities 16 in which the extensions 6 of the screw head 4 are pivotably received. The cavities 16 are substantially rectangular in cross-section, whereby the radial stops 6*b* of the extensions 6 of the screw head abut the support surfaces or stop surfaces 16*a* formed by the cavities 16 in any pivoted position. The cavities 16 in the first embodiment also have such a shape, but may be formed smaller.

Figure 7:
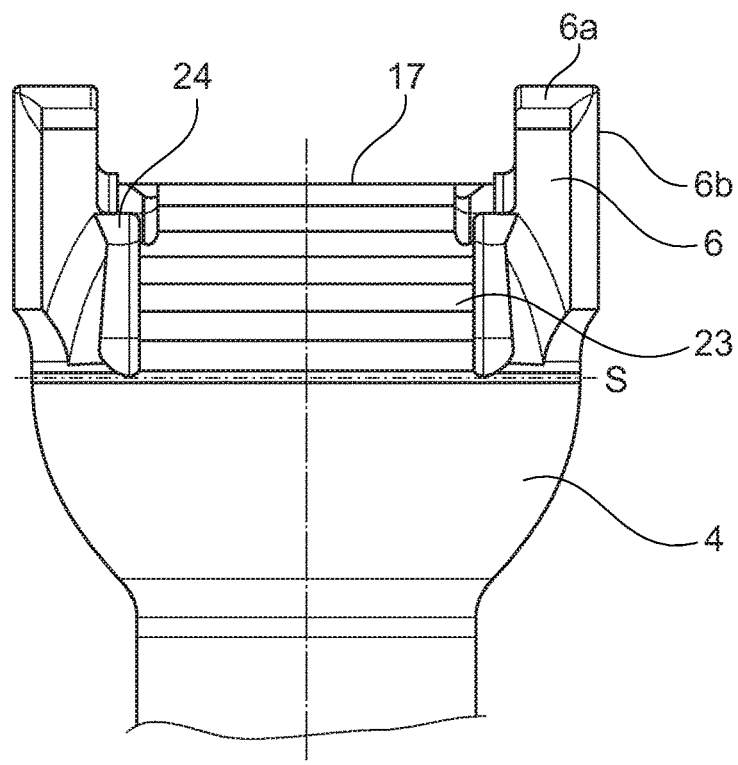
FIG. 7 is a side view of a screw head according to a third embodiment of the invention.

FIG. 7 shows a side view of a screw head 4 according to a third embodiment of the invention. Compared with the pedicle screw according to the first and second embodiment, the pedicle screw 1 according to this embodiment is designed to transmit particularly high forces and is therefore designed to be particularly stable. In the following, the special features and differences of this embodiment compared to the other two embodiments, in particular the first embodiment, are discussed, wherein the same reference signs are used for similar features.

This screw head 4 is also essentially ball-shaped/spherical and forms a proximal front surface 17, in which a tool receptacle or a channel may be embedded. Furthermore, a proximal half of the spherical surface of the screw head 4 is provided with cannelures or ribs 23. Due to these forms, the screw head 4 is not freely pivotable about the pivot axis S relative to the insertion sleeve 8, but can be locked in a specific position or pivot position via the ribs 23. Furthermore, the extensions 6 are very large. That is, they project in the screw-diametrical direction beyond the outer circumference of the spherical base body of the screw head 4, so that a screw-diametrical extension of the extensions 6 is greater than the diameter of the spherical base body of the screw head 4. In addition, the extensions 6 project in the longitudinal screw direction beyond the proximal front surface 17 of the screw head 4. In this way, the extensions 6 may form additional support surfaces on their radial inner side, which, similar to the support lugs 18 of the second embodiment, are supported on corresponding surfaces of the insertion sleeve 8 in order to achieve additional stability of the pedicle screw against transverse pivoting. If required, the extensions 6 may also be used to clamp/span the insertion sleeve 8 between them.

Radially within the extensions 6, the spherical screw head 4 is cylindrically recessed, e.g. by milling, so as not to impede a pivoting movement of the receiving sleeve 2 between the extensions 6 of the screw head 4. If required, this may provide a further bearing surface 24 in addition to the bearing surfaces 6*a* formed by the extensions 6. In summary, the third embodiment is essentially a combination of the first and second embodiments, which provides a particularly high degree of stability against transverse pivoting.

FIG. 8 shows a perspective view of the insertion sleeve 8 according to the third embodiment of the invention. It is clearly visible that the recesses 10 of the insertion sleeve 8 are significantly deeper than those of the first and second embodiment, so that the large extensions 6 have room therein. Furthermore, the recesses 10 are offset radially outwards, creating a step in each case. The radially inner, more distal part of each step is also cylindrically recessed so as not to impede a pivoting movement of the receiving sleeve 2 between the extensions 6 of the screw head 4. In addition, if required, additional bearing surfaces 25 may be formed by these more distal parts of the steps, which are adapted to interact with the bearing surfaces 24 of the screw head 4 in the manner of a plain bearing.

Figure 9:
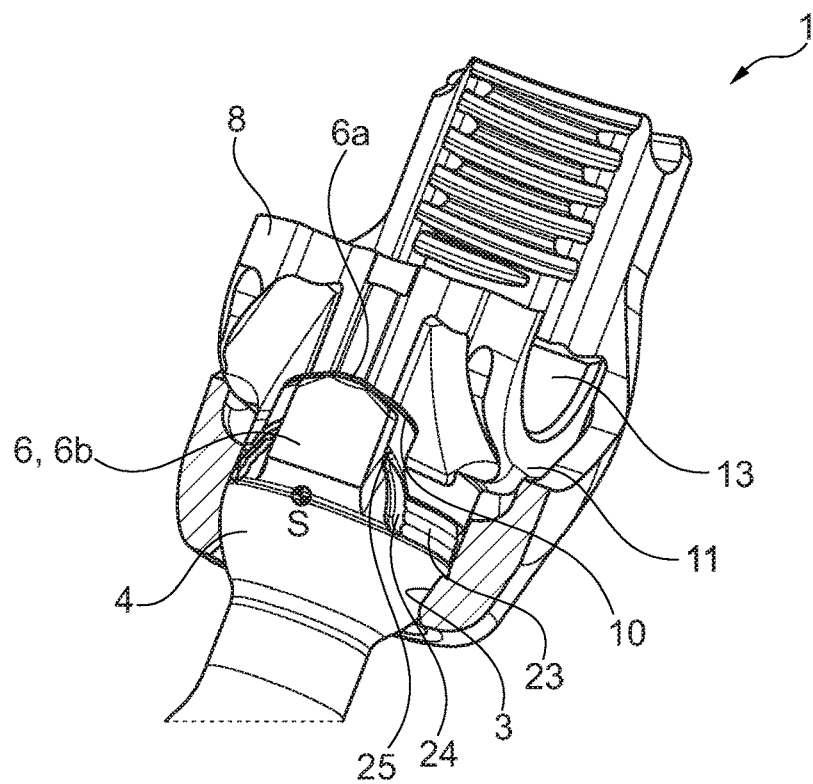
FIG. 9 shows a partial perspective sectional view of the pedicle screw according to the third embodiment.

FIG. 9 shows a perspective, partial sectional view of the assembled pedicle screw 1 according to the third embodiment of the invention. It is clearly visible how the receiving surface 9 of the insertion sleeve 8 sits on the ribs 23 of the screw head 4 and how the extensions 6 engage in the recesses 10 of the insertion sleeve 8 to form pairs of active surfaces both via the bearing surfaces 6*a* of the extensions 6 with the recesses 10 of the insertion sleeve 8 in the longitudinal screw direction and via the radially inner support surfaces of the extensions 6 with the steps formed by the recesses 10 in the screw-diametrical direction.

Figure 10:
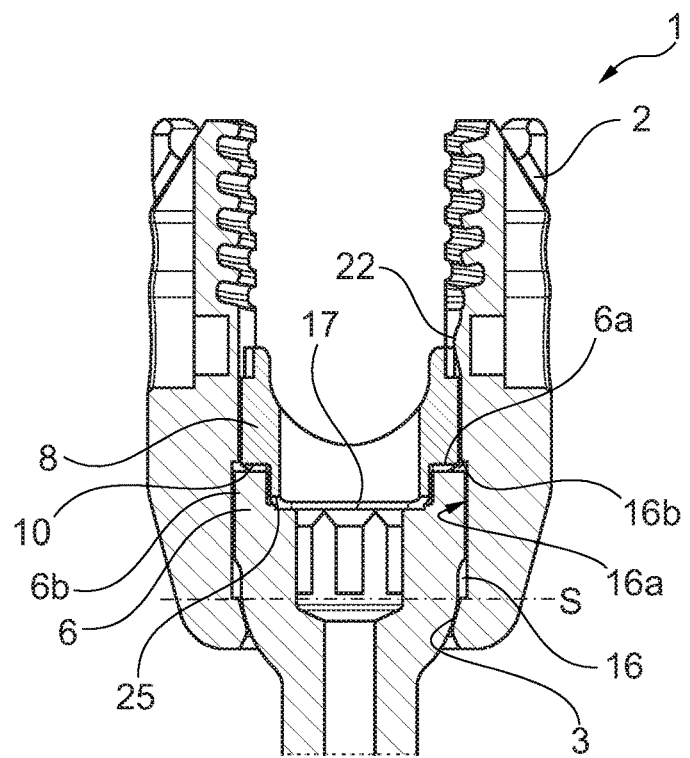
FIG. 10 shows a longitudinal sectional view of the pedicle screw according to the third embodiment of the invention.

FIG. 10 shows a longitudinal section of an assembled pedicle screw according to the third embodiment, which reveals a further specialty of the present embodiment. It can be seen that the cavities 16 form an undercut in the receiving sleeve 2. That is, the cavities 16 provide not only the screw-diametrically oriented support surface or stop surface 16*a*, but also a proximal, screw-longitudinally oriented additional support surface 16*b*, against which the bearing surfaces 6*a* of the extensions 6 of the screw head 4 come into contact. This ensures that the screw head 4 is also supported in the longitudinal screw direction not only on the insertion sleeve 8 but also directly on the receiving sleeve 2. This means that according to this embodiment, the screw head 4 is directly supported by the receiving sleeve 2 and the insertion sleeve 8 both in the proximal and in the screw-diametrical direction and maximum stability against transverse pivoting is achieved. The cavity 16 may be square in cross-section so that the screw head can also be used transversely and the same receiving sleeve can be used for differently oriented polyaxial pedicle screws.

The invention claimed is:

1. A polyaxial pedicle screw comprising:
a screw shaft;
a screw head with a substantially spherical shape formed in one piece at a proximal end of the screw shaft;
a receiving sleeve or tulip in which the screw head is mounted;
an insertion sleeve inserted into the receiving sleeve or tulip, the insertion sleeve configured to be pressed against the screw head to fix a relative pivot position between the receiving sleeve or tulip and the screw shaft; and
two diametrically opposite pivot guide units or pivot restriction units, which each have at least one extension projecting radially and proximally in a longitudinal screw direction from the substantially spherical shape of the screw head, wherein the extensions form stops on their respective radial outer surfaces, and are positioned in such a way that they permit relative pivoting of the screw shaft and the tulip or receiving sleeve only in a first pivot plane and that, in the event of relative pivoting in a second pivot plane, they are supported to be stopped at a radially inner circumferential side of the tulip or receiving sleeve.

2. The polyaxial pedicle screw according to claim 1, wherein pivoting of the screw shaft relative to the receiving sleeve or tulip in the first pivot plane by at least +/−22°.

3. The polyaxial pedicle screw according to claim 1, wherein the receiving sleeve or tulip has, offset in the circumferential direction by 90° with respect to the extensions, slots for receiving a connecting rod, via which the polyaxial pedicle screw is connectable to one or more other pedicle screws.

4. The polyaxial pedicle screw according to claim 1, wherein a diameter of the proximal bearing surfaces of the extensions is smaller than a diameter of the substantially spherical shape of the screw head.

5. The polyaxial pedicle screw according to claim 1, wherein the radial outer surfaces of the extensions extend in the longitudinal screw direction.

6. The polyaxial pedicle screw according to claim 1, wherein the radial outer surfaces form part of a lateral surface of a cylinder extending in the longitudinal screw direction.

7. The polyaxial pedicle screw according to claim 1, wherein the radial outer surfaces are respectively supported at flat lateral wall surfaces formed on the radially inner circumferential side of the tulip or receiving sleeve.

8. The polyaxial pedicle screw according to claim 1, wherein the radial outer surfaces extend essentially parallel to the first pivot plane.

9. The polyaxial pedicle screw according to claim 1, wherein the extensions extend beyond the substantially spherical shape of the screw head in a proximal direction.

10. The polyaxial pedicle screw according to claim 1, wherein:
the insertion sleeve comprises a hollow-spherical receiving surface arranged to press against a proximal end of the screw head, and recesses extending proximally from the hollow-spherical receiving surface and defining flat sides; and
the screw head comprises screw-radially flat surfaces configured to contact the flat sides.

11. The polyaxial pedicle screw according to claim 10, wherein the screw-radially flat sides are outer sides with respects to the radial direction.

12. The polyaxial pedicle screw according to claim 11, wherein each screw-radially flat surface is defined on a support lug extending proximally beyond the outer diameter of the substantially spherical shape of the screw head.

13. The polyaxial pedicle screw according to claim 10, wherein the screw-radially flat sides are inner sides with respect to the radial direction.

14. The polyaxial pedicle screw according to claim 13, wherein each screw-radially flat surface is defined on a respective one of the extensions.

15. The polyaxial pedicle screw according to claim 1, wherein the screw head comprises cannelures or ribs against which the insertion sleeve is configured to be pressed.

16. A polyaxial pedicle screw comprising:
a screw shaft;
a screw head with a substantially spherical shape formed in one piece at a proximal end of the screw shaft;
a receiving sleeve or tulip in which the screw head is mounted;
an insertion sleeve inserted into the receiving sleeve or tulip, the insertion sleeve configured to be pressed against the screw head to fix a relative pivot position between the receiving sleeve or tulip and the screw shaft; and
two diametrically opposite pivot guide units or pivot restriction units, which each have at least one extension projecting radially and in a longitudinal screw direction from the substantially spherical shape of the screw head, wherein the extensions form stops on their respective radial outer surfaces, and are positioned in such a way that they permit relative pivoting of the screw shaft and the tulip or receiving sleeve only in a first pivot plane and that, in the event of relative pivoting in a second pivot plane, they are supported to be stopped at a radially inner circumferential side of the tulip or receiving sleeve,
wherein the extensions proximally form partially cylindrical bearing surfaces which guide the relative pivoting of the screw shaft and the tulip or receiving sleeve in the first pivot plane and which are guided in a proximal direction on frontal or distal, correspondingly partially cylindrical recesses of the insertion sleeve.

17. The polyaxial pedicle screw according to claim 16, wherein the tulip or receiving sleeve has, on an inner circumferential surface, at least two cavities that are diametrically opposed and sufficiently large to accommodate the extensions in any pivoted position.

18. The polyaxial pedicle screw according to claim 17, wherein the extensions project screw-radially outwards beyond an outer diameter of the substantially spherical shape of the screw head.

19. The polyaxial pedicle screw according to claim 18, wherein the cavities are formed by an undercut recessed in an inner circumferential wall of the receiving sleeve or tulip.

20. The polyaxial pedicle screw according to claim 19, wherein the extensions are supported in the undercut formed by the cavities in the receiving sleeve or tulip both screw-diametrically outwards and in the longitudinal screw direction.

21. The polyaxial pedicle screw according to claim 19, wherein the undercut has a rectangular cross-section.

22. The polyaxial pedicle screw according to claim 18, wherein the extensions are each flat screw-radially on an inside and are guided on corresponding surfaces of the recesses.

23. The polyaxial pedicle screw according to claim 18, wherein the extensions project proximally beyond the outer diameter of the substantially spherical shape of the screw head.

24. A polyaxial pedicle screw comprising:
a screw shaft;
a screw head with a substantially spherical shape formed in one piece at a proximal end of the screw shaft;
a receiving sleeve or tulip in which the screw head is mounted;
an insertion sleeve inserted into the receiving sleeve or tulip, the insertion sleeve configured to be pressed against the screw head to fix a relative pivot position between the receiving sleeve or tulip and the screw shaft; and
two diametrically opposite pivot guide units or pivot restriction units, which each have at least one extension projecting radially and in a longitudinal screw direction from the substantially spherical shape of the screw head, wherein the extensions form stops on their respective radial outer surfaces, and are positioned in such a way that they permit relative pivoting of the screw shaft and the tulip or receiving sleeve only in a first pivot plane and that, in the event of relative pivoting in a second pivot plane, they are supported to be stopped at a radially inner circumferential side of the tulip or receiving sleeve,
wherein the screw head comprises support lugs which are screw-diametrically offset inwards with respect to the extensions and which project beyond the extensions in the proximal direction.

25. The polyaxial pedicle screw according to claim 24, wherein the support lugs form proximally partially cylindrical second bearing surfaces supported at frontal, correspondingly partially cylindrical slots of the insertion sleeve.

26. The polyaxial pedicle screw according to claim 25, wherein the support lugs are screw-radially flat on the outside and supported on corresponding side surfaces of the frontal, correspondingly partially cylindrical slots to block pivoting in the second pivot plane.

27. The polyaxial pedicle screw according to claim 26, wherein the support lugs are screw-radially flat on the inside and are supported on the corresponding side surfaces of the frontal, correspondingly partially cylindrical slots to block pivoting in the second pivot plane.

28. The polyaxial pedicle screw according to claim 24, wherein the support lugs are screw-radially flat and supported on corresponding side surfaces of slots of the insertion sleeve to block pivoting in the second pivot plane.

29. The polyaxial pedicle screw according to claim 24, wherein the support lugs are each flat screw-radially on an outside.

* * * * *